US009005594B2

(12) United States Patent
Hercouet et al.

(10) Patent No.: US 9,005,594 B2
(45) Date of Patent: *Apr. 14, 2015

(54) METHOD FOR LIGHTENING HUMAN KERATIN FIBERS USING AT LEAST ONE ANHYDROUS COMPOSITION, AT LEAST ONE ORGANIC AMINE, AND AT LEAST ONE OXIDIZING AGENT, AND DEVICE FOR USE THEREOF

(75) Inventors: Leïla Hercouet, Neuilly Plaisance (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 1029 days.

This patent is subject to a terminal disclaimer.

(21) Appl. No.: 12/339,781

(22) Filed: Dec. 19, 2008

(65) Prior Publication Data

US 2009/0162309 A1    Jun. 25, 2009

Related U.S. Application Data

(60) Provisional application No. 61/006,485, filed on Jan. 16, 2008.

(51) Int. Cl.
| A61Q 5/08 | (2006.01) |
| A61Q 5/00 | (2006.01) |
| A61K 8/41 | (2006.01) |
| A61K 8/44 | (2006.01) |

(52) U.S. Cl.
CPC ... *A61K 8/41* (2013.01); *A61K 8/44* (2013.01); *A61K 2800/31* (2013.01); *A61K 2800/88* (2013.01); *A61Q 5/08* (2013.01)

(58) Field of Classification Search
USPC ............................................ 8/405; 424/70.1
See application file for complete search history.

(56) References Cited

U.S. PATENT DOCUMENTS

| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,826,681 A | 5/1989 | Jacquet et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | de la Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |

(Continued)

FOREIGN PATENT DOCUMENTS

| CA | 1 268 421 | 5/1990 |
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |

(Continued)

OTHER PUBLICATIONS

Boone, L., The Petroleum Dictionary, University of Oklahoma Press, 1952.*
LookChem, poly{dimethyliminio)-1,1,6-hexanediylchloride (1:2)], pp. 1-2, accesses Mar. 7, 2011.
Copending U.S. Appl. No. 12/339,753, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.

(Continued)

*Primary Examiner* — Gina Justice
(74) *Attorney, Agent, or Firm* — The Marbury Law Group, PLLC

(57) ABSTRACT

A novel process for lightening human keratin fibers comprising applying to the fibers at least one anhydrous composition (A) comprising at least one fatty substance and at least one surfactant, at least one composition (B) comprising at least one organic amine having a pKb less than 12, and at least one composition (C) comprising at least one oxidizing agent and leaving the compositions on the fibers for a period of time sufficient to lighten the fibers; and a multi-compartment device or kit, wherein at least one first compartment comprises the at least one anhydrous composition (A), at least one second compartment comprises the at least one composition (B), and at least one third compartment comprises the at least one composition (C).

16 Claims, No Drawings

(56) References Cited

U.S. PATENT DOCUMENTS

| | | |
|---|---|---|
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard |
| 7,799,095 B2 | 9/2010 | Mario et al. |
| 7,988,737 B2 | 8/2011 | Hercouet et al. |
| 2002/0189034 A1* | 12/2002 | Kitabata et al. .................. 8/405 |
| 2003/0064494 A1 | 4/2003 | Kumar et al. |
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0172771 A1 | 9/2004 | Cottard et al. |
| 2004/0181883 A1 | 9/2004 | Legrand et al. |
| 2004/0221400 A1 | 11/2004 | Cotteret et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |
| 2010/0162492 A1 | 7/2010 | Hercouet et al. |
| 2010/0175705 A1 | 7/2010 | Hercouet et al. |
| 2010/0186177 A1 | 7/2010 | Hercouet et al. |
| 2010/0199441 A1 | 8/2010 | Hercouet et al. |

FOREIGN PATENT DOCUMENTS

| | | |
|---|---|---|
| DE | 197 54 281 | 6/1999 |
| DE | 198 15 338 | 9/1999 |
| DE | 198 42 071 | 3/2000 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |

(56) References Cited

FOREIGN PATENT DOCUMENTS

| | | |
|---|---|---|
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 20 05 076, dated Aug. 6, 1970.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.

(56) References Cited

OTHER PUBLICATIONS

French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
French Search Report for FR 07/60274, dated Aug. 20, 2008.
Copending U.S. Appl. No. 12/976,093, filed Dec. 22, 2010.
Copending U.S. Appl. No. 12/976,124, filed Dec. 22, 2010.
Copending U.S. Appl. No. 12/976,150, filed Dec. 22, 2010.
Copending U.S. Appl. No. 12/976,173, filed Dec. 22, 2010.
English language abstract of DE 198 42 071, Mar. 16, 2000.
English language Abstract of WO 2007/006418, dated Jan. 18, 2007.
European Search Report for EP 10 15 5935, dated Oct. 8, 2010.
European Search Report for EP 10 19 5262, dated Apr. 1, 2011.
French Search Report for FR 09/59388, dated Aug. 3, 2010.
French Search Report for FR 09/59391, dated Sep. 16, 2010.
French Search Report for FR 09/59433, dated Sep. 24, 2010.
French Search Report for FR 09/59434, dated Sep. 24, 2010.
LookChem, poly[(dimethyliminio)-1,1,6-hexanediylchloride (1:2)], pp. 1-2, accesses Mar. 7, 2011.
Notice of Allowance mailed Apr. 1, 2011, in U.S. Appl. No. 12/642,506.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/3976,173, dated Aug. 29, 2011.
Notice of Allowance mailed in U.S. Appl. No. 12/642,468, dated Sep. 7, 2011.
Notice of Allowance mailed Jan. 28, 2011, in U.S. Appl. No. 12/642,592.
Notice of Allowance mailed Mar. 9, 2011, in U.S. Appl. No. 12/642,473.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Office Action mailed Dec. 17, 2010, in co-pending U.S. Appl. No. 12/642,451.
Office Action mailed Mar. 16, 2011, in co-pending U.S. Appl. No. 12/642,583.
Office Action mailed Mar. 29, 2011, in co-pending U.S. Appl. No. 12/642,468.
Office Action mailed Nov. 22, 2010, in co-pending U.S. Appl. No. 12/642,593.
P.R. Canterbery et al., International Cosmetic Ingredient Dictionary and Handbook, vol. 1, p. 759 (2002).
STIC Search Report for U.S. Appl. No. 12/976,173, dated May 13, 2011.
Ullmann's Encyclopedia of Industrial Chemistry, "Hair Preparations," Wiley-VCH Verlag GnbH & Co., KGaA, Weinheim, p. 20 (2006).

* cited by examiner

METHOD FOR LIGHTENING HUMAN KERATIN FIBERS USING AT LEAST ONE ANHYDROUS COMPOSITION, AT LEAST ONE ORGANIC AMINE, AND AT LEAST ONE OXIDIZING AGENT, AND DEVICE FOR USE THEREOF

This application claims benefit of U.S. Provisional Application No. 61/006,485, filed Jan. 16, 2008, the contents of which are incorporated herein by reference. This application also claims benefit of priority under 35 U.S.C. §119 to French Patent Application No. FR 0760274, filed Dec. 21, 2007, the contents of which are also incorporated herein by reference.

Disclosed herein is a process for lightening human keratin fibers using at least one anhydrous composition (A) comprising at least one fatty substance and at least one surfactant, at least one composition (B) comprising at least one organic amine having a pKb less than 12 at 25° C., and at least one composition (C) comprising at least one oxidizing agent.

The present disclosure also relates to a multi-compartment device or kit, comprising at least one first compartment comprising the abovementioned at least one anhydrous composition (A), at least one second compartment comprising the at least one composition (B), and at least one third compartment comprising the at least one composition (C).

Processes for lightening human keratin fibers generally involve using an aqueous composition comprising at least one oxidizing agent, under alkaline pH conditions in the majority of cases. This oxidizing agent has the role of degrading the melanin of the hair, which, depending on the nature of the oxidizing agent present, leads to a more or less pronounced lightening of the fibers. Thus, for relatively weak lightening, the oxidizing agent is generally hydrogen peroxide. When greater lightening is sought, use may be made of peroxygenated salts, for instance persulfates, in the presence of hydrogen peroxide.

One difficulty may arise from the fact that the lightening process is performed under alkaline conditions, and the alkaline agent most commonly used is aqueous ammonia. Aqueous ammonia is frequently used in processes of this type. The reason for this is that it allows the pH of the composition to be adjusted to an alkaline pH to enable degradation of the oxidizing agent. In addition, this agent may also cause swelling of the keratin fiber, with opening of the scales, which can promote the penetration of the oxidizing agent into the fiber, and thus may increase the efficacy of the reaction.

However, this basifying agent can be very volatile, which users may find disagreeable due to the characteristic strong, rather unpleasant odor of ammonia that is given off during the process.

Furthermore, the amount of ammonia given off can require the use of higher amounts than necessary in order to compensate for this loss. That may have consequences for the user, who not only may remain inconvenienced by the odor, but may also be confronted with greater risks of intolerance, for instance irritation of the scalp such as stinging.

The option of replacing all or some of the aqueous ammonia with at least one other standard basifying agents frequently does not lead to compositions that can be as efficient as those based on aqueous ammonia, for example, since those basifying agents do not always afford sufficient lightening of pigmented fibers in the presence of the oxidizing agent.

Thus, there is a need in the art for processes for lightening human keratin fibers which do not have at least one of the drawbacks of those associated with existing compositions, due to the presence of large amounts of aqueous ammonia, but at the same time maintain at least some of the efficiency, with respect to the lightening and the homogeneity of said lightening.

Accordingly, one aspect of the present disclosure is a process for lightening human keratin fibers, comprising:
applying to the fibers:
at least one anhydrous composition (A) comprising at least one fatty substance and at least one surfactant;
at least one composition (B) comprising at least one organic amine having a pKb less than 12 at 25° C.; and
at least one composition (C) comprising at least one oxidizing agent; and
leaving the compositions on the fibers for a period of time sufficient to lighten the fibers.

The present disclosure also relates to a multi-compartment device or kit comprising, in at least one first compartment, at least one anhydrous composition (A) comprising at least one fatty substance and at least one surfactant, in at least one second compartment at least one composition (B) comprising at least one organic amine having a pKb less than 12 at 25° C., and in at least one third compartment at least one composition (C) comprising at least one oxidizing agent.

At least one other characteristic and benefit of the present disclosure may emerge more clearly upon reading the description and the non-limiting examples that follow.

In the text of the present disclosure, unless otherwise indicated, the limits of a range of values are included in that range.

The human keratin fibers treated by the process according to the present disclosure include hair.

The at least one anhydrous composition (A) can, for example, have a water content of less than 5% by weight, further for example less than or equal to 2% by weight and further for example less than or equal to 1% by weight relative to the weight of said composition. The water may also be in the form of bound water, for instance the water of crystallization of salts, or traces of water absorbed by the starting materials used in the preparation of the compositions according to the present disclosure.

In addition, the at least one composition (A) does not comprise any direct dye or oxidation dye precursor (bases and couplers) usually used for the dyeing of human keratin fibers, or, if it does contain any, they are present in a total amount not exceeding 0.005% by weight relative to the weight of the at least one anhydrous composition (A) and of the at least one composition (C) comprising the oxidizing agent. In such an amount, only the composition would be dyed, i.e. no dyeing effect on the keratin fibers would be observed.

For example, the at least one anhydrous composition (A) does not comprise any oxidation bases such as para-phenylenediamines, bis(phenyl)alkylenediamines, para-aminophenols, ortho-aminophenols, or heterocyclic bases and the acid-addition salts thereof. For further example, the at least one anhydrous composition (A) also does not comprise any couplers, for instance meta-phenylenediamines, meta-aminophenols, meta-diphenols, naphthalene-based couplers, or heterocyclic couplers, and also the addition salts thereof. Further still for example, the at least one anhydrous composition (A) does not comprise any nonionic or ionic, as well as cationic or anionic, direct dyes, for instance azo, methine, carbonyl, azine, nitro (hetero)aryl; tri(hetero)arylmethane; porphyrin; phthalocyanin direct dyes; or natural direct dyes, alone or as mixtures.

As mentioned above, the at least one anhydrous composition (A) according to the present disclosure comprises at least one fatty substance.

As used herein, "fatty substance" means an organic compound that is insoluble in water at room temperature (25° C.)

and at atmospheric pressure (760 mmHg) (solubility of less than 5%, for example less than 1%, and further for example less than 0.1%). In addition, the at least one fatty substance is soluble in organic solvents, for instance chloroform, ethanol, or benzene, under the same temperature and pressure conditions.

According to the present disclosure, the at least one fatty substance can be chosen from compounds that are liquid or pasty at room temperature and at atmospheric pressure.

For example, the at least one fatty substance may be chosen from alkanes, fatty alcohols, fatty acids, fatty acid esters, fatty alcohol esters, mineral oils, plant oils, animal oils, synthetic oils, silicones, and waxes.

It is recalled that, for the purposes of the present disclosure, the fatty alcohols, fatty esters, and fatty acids can contain at least one group chosen from linear and branched, saturated and unsaturated hydrocarbon-based groups containing 6 to 30 carbon atoms, optionally substituted, for example, with at least one hydroxyl group (for example 1 to 4). If they are unsaturated, these compounds may comprise one to three conjugated or nonconjugated carbon-carbon double bonds.

For example, in at least one embodiment, the alkane groups comprising from 6 to 30 carbon atoms, are linear. In at least one embodiment the alkane groups can be chosen from hexane and dodecane.

As oils that may be used in the composition (A) of the present disclosure, non-limiting examples that may be mentioned include:

hydrocarbon-based oils of animal origin, such as perhydrosqualene;

hydrocarbon-based oils of plant origin, such as liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Séarineries Dubois or those sold under the names MIGLYOL® 810, 812, and 818 by the company Dynamit Nobel, jojoba oil, and shea butter oil;

linear and branched hydrocarbons of mineral or synthetic origin, such as volatile or nonvolatile liquid paraffins, and derivatives thereof, petroleum jelly, liquid petroleum jelly, polydecenes, hydrogenated polyisobutene such as PARLEAM®, isoparaffins, for instance isohexadecane, and isodecane;

linear and branched, saturated and unsaturated fatty alcohols comprising from 8 to 30 carbon atoms, for instance cetyl alcohol, stearyl alcohol, and the mixture thereof (cetylstearyl alcohol), octyidodecanol, 2-butyloctanol, 2-hexyldecanol, 2-undecylpentadecanol, oleyl alcohol, or linoleyl alcohol;

partially hydrocarbon-based and/or silicone-based fluoro oils, for instance those described in Japanese Publication No. JP-A-2-295 912; fluoro oils that may also be mentioned by way of non-limiting example include perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The waxes may, by way of non-limiting example, be chosen from carnauba wax, candelilla wax, esparto grass wax, paraffin wax, ozokerites, plant waxes such as olive wax, rice wax, hydrogenated jojoba wax, or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the present disclosure include marine waxes such as the product sold by the company Sophim under the reference M82, and polyethylene waxes or polyolefin waxes in general.

The fatty acids may, by way of non-limiting example, be saturated or unsaturated and contain from 6 to 30 carbon atoms, for example from 9 to 30 carbon atoms. Further for example, the fatty acids may be chosen from myristic acid, palmitic acid, stearic acid, behenic acid, oleic acid, linoleic acid, linolenic acid, and isostearic acid.

The esters may be chosen from esters of saturated and unsaturated, linear and branched $C_1$-$C_{26}$ aliphatic mono- and polyacids and of saturated and unsaturated, linear and branched $C_1$-$C_{26}$ aliphatic mono- and polyalcohols, the total carbon number of the esters being greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl, or stearyl myristate, hexyl stearate, butyl stearate, isobutyl stearate; dioctyl malate, hexyl laurate, 2-hexyldecyl laurate.

By way of further non-limiting example, esters chosen from esters of $C_4$-$C_{22}$ dicarboxylic and tricarboxylic acids and of $C_1$-$C_{22}$ alcohols and esters of mono-, di-, and tricarboxylic acids and of $C_2$-$C_{26}$ di-, tri-, tetra-, and pentahydroxy alcohols may also be used.

For example, non-limiting mention may be made of the following: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyidodecyl citrate; trioleyl citrate; propylene glycol dioctanoate; neopentyl glycol diheptanoate; diethylene glycol diisononanoate; and polyethylene glycol distearates.

Further examples of esters that may be used in composition (A) according to the present disclosure, include ethyl, isopropyl, myristyl, cetyl, or stearyl palmitate, 2-ethylhexyl palmitate, 2-octyldecyl palmitate, alkyl myristates such as isopropyl, butyl, cetyl, or 2-octyldodecyl myristate, hexyl stearate, butyl stearate, isobutyl stearate, dioctyl malate, hexyl laurate, 2-hexyldecyl laurate, isononyl isononanoate, or cetyl octanoate.

The at least one fatty substance may also comprise, as fatty ester, sugar esters and diesters of $C_6$-$C_{30}$, for example $C_{12}$-

$C_{22}$ fatty acids. As used herein, the term "sugar" means oxygen-bearing hydrocarbon-based compounds comprising several alcohol functional groups, with or without aldehyde or ketone functional groups, and which comprise at least 4 carbon atoms. These sugars may be monosaccharides, oligosaccharides, or polysaccharides.

Non-limiting examples of suitable sugars that may be mentioned include sucrose (or saccharose), glucose, galactose, ribose, fructose, maltose, mannose, arabinose, xylose, and lactose, and derivatives thereof, including alkyl derivatives, such as methyl derivatives, for instance methylglucose.

The sugar esters of fatty acids may, by way of non-limiting example, be chosen from esters and mixtures of esters of sugars described previously and esters of linear and branched, saturated and unsaturated $C_6$-$C_{30}$, for example $C_{12}$-$C_{22}$ fatty acids. If they are unsaturated, these compounds may comprise one to three conjugated or nonconjugated carbon-carbon double bonds.

By way of further non-limiting example, the esters according to the present disclosure may also be chosen from mono-, di-, tri-, tetraesters, and polyesters, and mixtures thereof.

These esters may be chosen, by way of non-limiting example, from oleates, laurates, palmitates, myristates, behenates, cocoates, stearates, linoleates, linolenates, caprates, and arachidonates, or mixtures thereof such as, oleo-palmitate, oleo-stearate, and palmito-stearate mixed esters.

In at least one embodiment, monoesters and/or diesters are used, for example sucrose, glucose, or methylglucose, mono- or dioleates, stearates, behenates, oleopalmitates, linoleates, linolenates, and oleostearates. Non-limiting mention may be made of the product sold under the name GLUCATE® DO by the company Amerchol, which is a methylglucose dioleate.

Non-limiting examples of esters or mixtures of esters of sugar and of fatty acid that may also be mentioned include:

the products sold under the names F160, F140, F110, F90, F70, and SL40 by the company Crodesta, which are, respectively, sucrose palmitostearates formed from 73% monoester and 27% diester and triester, from 61% monoester and 39% diester, triester, and tetraester, from 52% monoester and 48% diester, triester, and tetraester, from 45% monoester and 55% diester, triester, and tetraester, from 39% monoester and 61% diester, triester, and tetraester, and sucrose monolaurate;

the products sold under the name Ryoto Sugar Esters, for example B370, which is sucrose behenate formed from 20% monoester and 80% di-triester-polyester;

the sucrose mono-dipalmito-stearate sold by the company Goldschmidt under the name TEGOSOFT® PSE.

The silicones that may be used in composition (A) of the present disclosure include volatile, nonvolatile, cyclic, linear, and branched silicones, which are unmodified or modified with organic groups, having a viscosity from $5\times10^{-6}$ to 2.5 $m^2/s$ at 25° C., for example from $1\times10^{-5}$ to 1 $m^2/s$.

The silicones that may be used in accordance with the present disclosure may, by way of non-limiting example, be in the form of oils, waxes, resins, or gums.

For example, the silicone may be chosen from polydialkylsiloxanes, further for example polydimethylsiloxanes (PDMS), and organomodified polysiloxanes comprising at least one functional group chosen from poly(oxyalkylene) groups, amino groups, and alkoxy groups.

The organopolysiloxanes are defined in greater detail in Walter Noll's "Chemistry and Technology of Silicones" (1968) Academic Press. They can be volatile or nonvolatile. When they are volatile, the silicones may, for example, be chosen from those having a boiling point of between 60° C. and 260° C., and further for example from:

(i) cyclic polydialkylsiloxanes containing from 3 to 7 silicon atoms, for example 4 to 5 silicon atoms. These are, for example, octamethylcyclotetrasiloxane sold further for example under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of the formula:

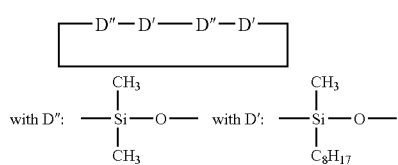

Non-limiting mention may also be made of mixtures of cyclic polydialkylsiloxanes with organosilicon compounds, such as the mixture of octamethylcyclotetrasiloxane and tetra-trimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ $m^2/s$ at 25° C. A non-limiting example is decamethyltetrasiloxane sold, for example under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

In at least one embodiment, nonvolatile polydialkylsiloxanes, polydialkylsiloxane gums, and resins, polyorganosiloxanes modified with organofunctional groups above, and mixtures thereof, may be used in composition (A) according to the present disclosure.

Further for example, polydialkylsiloxanes including polydimethylsiloxanes comprising trimethylsilyl end groups may be used.

The viscosity of the silicones is measured, for example, at 25° C. according to ASTM standard 445 Appendix C.

Among these polydialkylsiloxanes, non-limiting mention may be made of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60,000 $mm^2/s$;

the VISCASIL® oils from General Electric and certain oils of the SF series (SF 96, SF 18) from General Electric.

Non-limiting mention may also be made of polydimethylsiloxanes containing dimethylsilanol end groups known under the name Dimethiconol (CTFA), such as the oils of the 48 series from the company Rhodia.

In this category of polydialkylsiloxanes, non-limiting mention may also be made of the products sold under the names ABIL WAX® 9800 and 9801 by the company Goldschmidt, which are poly($C_1$-$C_{20}$)dialkylsiloxanes.

The silicone gums that can be used in composition (A) in accordance with the present disclosure may, for example, be polydialkylsiloxanes, further for example polydimethylsiloxanes with high number-average molecular masses ranging from 200,000 to 1,000,000, used alone or as a mixture in a solvent. This solvent may, by way of non-limiting example, be chosen from volatile silicones, polydimethylsiloxane (PDMS) oils, poly-phenylmethylsiloxane (PPMS) oils, isoparaffins, polyisobutylenes, methylene chloride, pentane, dodecane, and tridecane, and mixtures thereof.

By way of further non-limiting example, mixtures that can be used in accordance with the present disclosure are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, for example of a PDMS gum and a PDMS oil, such as the product SF 1236 from the company General Electric. The product SF 1236 is a mixture of an SE 30 gum defined above, having a viscosity of 20 $m^2/s$, and an SF 96 oil, with a viscosity of $5 \times 10^{-6}$ $m^2/s$. This product may, for example, contain 15% SE 30 gum and 85% SF 96 oil.

The organopolysiloxane resins that can be used in composition (A) in accordance with the present disclosure include, by way of non-limiting example, crosslinked siloxane systems comprising the following units:

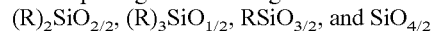

wherein R is a hydrocarbon-based group comprising 1 to 16 carbon atoms. Among such products, are those, for example, wherein R is a $C_1$-$C_4$ lower alkyl radical, further for example methyl.

Among these resins, further non-limiting mention may be made of the product sold under the name Dow Corning 593 or those sold under the names Silicone Fluid SS 4230 and SS 4267 by the company General Electric, which are silicones of dimethyl/trimethyl siloxane structure.

Non-limiting mention may also be made of the trimethyl siloxysilicate type resins sold, for example under the names X22-4914, X21-5034, and X21-5037 by the company Shin-Etsu.

The organomodified silicones that can be used in accordance with the present disclosure are silicones as defined above, comprising in their structure at least one organofunctional group attached via a hydrocarbon-based radical.

In addition to the silicones described above, the organomodified silicones may, by way of non-limiting example, be polydiarylsiloxanes, for example polydiphenylsiloxanes, and polyalkylarylsiloxanes functionalized with the organofunctional groups mentioned previously.

The polyalkylarylsiloxanes may, for example, be chosen from linear and branched polydimethyl/methylphenylsiloxanes and polydimethyl/diphenylsiloxanes with a viscosity ranging from $1 \times 10^{-5}$ to $5 \times 10^{-2}$ $m^2/s$ at 25° C.

Among these polyalkylarylsiloxanes, non-limiting examples that may be mentioned include the products sold under the following names:

the SILBIONE® oils of the 70 641 series from Rhodia;
the oils of the RHODOURSIL® 70 633 and 763 series from Rhodia;

the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250, and SF 1265.

Among the organomodified silicones that may be used in composition (A) according to the present disclosure, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77, and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, $C_1$-$C_4$ aminoalkyl groups;

alkoxylated groups such as the product sold under the name Silicone Copolymer F-755 by SWS Silicones, and ABIL WAX® 2428, 2434, and 2440 by the company Goldschmidt.

The at least one fatty substance in composition (A) according to the present disclosure may, for example, be a liquid at a temperature of 25° C. and at atmospheric pressure.

For example, the at least one fatty substance may be chosen from liquid petroleum jelly, polydecenes, and liquid esters.

The at least one fatty substance is present in the anhydrous composition (A) in a total amount ranging from 10% to 99% by weight, for example from 20% to 90% by weight, and further for example from 25% to 80% by weight relative to the weight of the anhydrous composition.

The at least one anhydrous composition (A) also comprises at least one surfactant.

For example, the at least one surfactant may be chosen from nonionic surfactants and anionic surfactants.

The anionic surfactants may, by way of further example, be chosen from the salts (for example alkali metal salts, further for example sodium salts, ammonium salts, amine salts, amino alcohol salts, or alkaline-earth metal salts such as magnesium salts) of the following compounds:

alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefin sulfonates, paraffin sulfonates;
alkyl phosphates, alkyl ether phosphates;
alkylsulfosuccinates, alkyl ether sulfosuccinates, alkylamidesulfosuccinates; alkylsulfosuccinates;
alkylsulfoacetates;
acylsarcosinates; acylisethionates; and N-acyltaurates;
salts of fatty acids such as oleic acid, ricinoleic acid, palmitic acid, or stearic acid, coconut oil acid or hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids, or of polyoxyalkylenated alkylamido ether carboxylic acids, for instance those comprising from 2 to 50 ethylene oxide groups;
and mixtures thereof.

Further by way of non-limiting example, the alkyl or acyl radical of these various compounds can comprise from 6 to 24 carbon atoms, for example from 8 to 24 carbon atoms, and the aryl radical can be chosen from phenyl and benzyl groups.

The nonionic surfactants may, by way of example, be chosen from monooxyalkylenated, polyoxyalkylenated, monoglycerolated, and polyglycerolated nonionic surfactants. The oxyalkylene units may be chosen from oxyethylene and oxypropylene units, and a combination thereof, for example oxyethylene units.

Non-limiting examples of oxyalkylenated nonionic surfactants that may be used in composition (A) according to the present disclosure include:

oxyalkylenated ($C_8$-$C_{24}$)alkylphenols, saturated, unsaturated, linear and branched, oxyalkylenated $C_8$-$C_{30}$ alcohols, saturated, unsaturated, linear, and branched, oxyalkylenated $C_8$-$C_{30}$ amides, saturated, unsaturated, linear, and branched, oxyalkylenated $C_8$-$C_{30}$ amines, esters of saturated, unsaturated, linear, and branched, $C_8$-$C_{30}$ acids and of polyethylene glycols, polyoxyethylenated esters of saturated, unsaturated, linear, and branched, $C_8$-$C_{30}$ acids and of sorbitol, saturated and unsaturated, oxyethylenated plant oils, condensates of ethylene oxide and/or of propylene oxide, inter alia, alone or as mixtures.

The at least one surfactant may contain a number of moles of ethylene oxide and/or of propylene oxide ranging, for example, from 1 to 50, further for example from 2 to 30.

In at least one embodiment, the at least one nonionic surfactant does not comprise any oxypropylene units.

In accordance with one another embodiment of the present disclosure, the oxyalkylenated nonionic surfactants may be chosen from oxyethylenated $C_8$-$C_{30}$ alcohols and oxyethylenated $C_8$-$C_{30}$ amines.

As non-limiting examples of monoglycerolated and polyglycerolated nonionic surfactants, monoglycerolated and polyglycerolated $C_8$-$C_{40}$ alcohols may be used.

Further for example, the monoglycerolated and polyglycerolated $C_8$-$C_{40}$ alcohols of the following formula may be used:

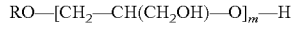

wherein R is chosen from linear and branched $C_8$-$C_{40}$, for example $C_8$-$C_{30}$, alkyl and alkenyl radicals, and m is a number ranging from 1 to 30, for example from 1 to 10.

As examples of compounds that are suitable in the context of the present disclosure, non-limiting mention may be made of lauryl alcohol containing 4 mol of glycerol (INCI name. Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may be a mixture of alcohols in the same way that the value of m is a statistical value, which means that, in a commercial product, several species of polyglycerolated fatty alcohol may coexist in the form of a mixture.

Among the monoglycerolated and polyglycerolated alcohols that may be used in composition (A) according to the present disclosure, mention may be made, for example, of the use of the $C_8$/$C_{10}$ alcohol containing 1 mol of glycerol, the $C_{10}$/$C_{12}$ alcohol containing 1 mol of glycerol, and the $C_{1-2}$ alcohol containing 1.5 mol of glycerol.

In at least one embodiment, the at least one surfactant present in the at least one anhydrous composition (A) is a nonionic surfactant.

The at least one surfactant is present in the at least one anhydrous composition (A), in a total amount ranging, for example, from 0.1% to 50% by weight, further for example from 0.5% to 30% by weight, relative to the weight of the at least one anhydrous composition (A).

The at least one anhydrous composition (A) may also contain at least one adjuvant conventionally used in hair dye compositions, such as anionic, cationic, nonionic, amphoteric, and zwitterionic polymers and mixtures thereof; mineral thickeners, for example fillers such as clays, talc; organic thickeners with, for example, anionic, cationic, nonionic, and amphoteric polymeric associative thickeners; antioxidants; penetrants; sequestrants; fragrances; dispersants; film-forming agents; ceramides; preserving agents; and opacifiers.

The above adjuvants may be present in an amount, for each of them, ranging from, for example, 0.01% to 20% by weight relative to the weight of composition (A).

According to at least one embodiment of the present disclosure, the at least one anhydrous composition (A) comprises at least one silica, for example of hydrophobic nature, for instance fumed silicas.

When present, the at least one silica may be present in an amount ranging, for example, from 1% to 30% by weight relative to the weight of the at least one anhydrous composition (A).

As indicated above, the at least one composition (B) employed in the process according to the present disclosure comprises at least one organic amine having a pKb at 25° C. less than 12, for example less than 10, and further for example less than 6. This is the pKb of the function of highest basicity.

In at least one embodiment of the present disclosure, the at least one organic amine is at least partially miscible with the at least one fatty substance present in the at least one anhydrous composition (A), at room temperature and atmospheric pressure. For example, the at least one organic amine may be totally soluble at a temperature of 25° C. and at atmospheric pressure (760 mmHg) in the at least one fatty substance. Further for example, the at least one fatty substance and the at least one organic amine may form a single phase at 25° C. and at atmospheric pressure.

By way of non-limiting example, the organic amine may comprise one or two functional groups chosen from primary, secondary, and tertiary amine functional groups, and at least one group chosen from linear and branched $C_1$-$C_8$ alkyl groups bearing at least one hydroxyl radical.

Among the organic amines that may be used in composition (B) of the present disclosure, non-limiting mention may be made of alkanolamines such as mono-, di, and trialkanolamines, comprising one to three identical or different $C_1$-$C_4$ hydroxyalkyl radicals.

Among the compounds of this type that may be used, non-limiting mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

The organic amines of formula:

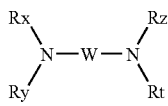

wherein W is chosen from $C_1$-$C_6$ alkylene residues optionally substituted with a hydroxyl group or a $C_1$-$C_6$ alkyl radical; Rx, Ry, Rz and Rt, which may be identical or different, are chosen from hydrogen atoms, and $C_1$-$C_6$ alkyl, $C_1$-$C_6$ hydroxyalkyl and $C_1$-$C_6$ aminoalkyl radicals, are also suitable for use.

Non-limiting examples of such amines that may be mentioned include 1,3-diaminopropane, 1,3-diamino-2-propanol, spermine, and spermidine.

By way of non-limiting example, the at least one organic amine in composition (B) according to the present disclosure may be chosen from amino acids.

For example, the amino acids that may be used are of natural or synthetic origin, in L, D, or racemic form, and comprise at least one acid functional group chosen for example from carboxylic acid, sulfonic acid, phosphonic acid, and phosphoric acid functional groups. The amino acids may be in their neutral or ionic form.

By way of further example, the amino acids may be amino acids comprising an additional amine functional group optionally included in a ring or in a ureido functional group.

Such amino acids may, by way of non-limiting example, be chosen from those of formula (I):

wherein R is a group chosen from:

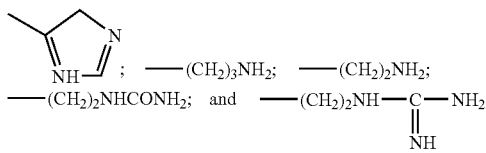

The compounds corresponding to formula (I) are histidine, lysine, arginine, ornithine, and citrulline.

By way of non-limiting example of amino acids that may be used in composition (B) of the present disclosure, mention may be made of aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine.

The at least one amino acid may be used as a mixture with at least one solid or pasty, including pulverulent, adjuvant. The at least one adjuvant may be chosen from clays, salts, anionic, nonionic, cationic, and zwitterionic surfactants; natural and synthetic thickeners; optionally modified starch, glass beads, silica, Nylon, alumina, titanium dioxide, zeolites, poly(methyl methacrylate) (PMMA), chitosan, maltodextrin, cyclodextrin, mono- and disaccharides, for instance glucose, sucrose, sorbitol, and fructose; zinc oxide, zirconium oxide, resin particles, for instance silicone and silica beads, talc, borosilicates, for example calcium borosilicate, polyethylene, cotton, polytetrafluoroethylene (PTFE), cellulose and its derivatives; superabsorbent compounds, magnesium carbonate, calcium carbonate, corn seeds, polydimethylsiloxane gums, polyacrylamide, porous hydroxyapatite, silk, collagen, sawdust, wrack powder, crosslinked polyvinylpyrrolidone, calcium alginate, active charcoal, and poly(vinylidene chloride/acrylonitrile) particles, for instance those sold under the general name EXPANCEL® by the company Akzo Nobel, for example EXPANCEL® WE and EXPANCEL® DE.

In at least one embodiment of the present disclosure, the at least one organic amine is chosen from amino acids. For example, the at least one amino acid, may be chosen from arginine, lysine, and histidine.

By way of non-limiting example, the at least one organic amine is chosen from organic amines of heterocyclic type. Besides histidine that has already been mentioned in the amino acids, mention may be made of pyridine, piperidine, imidazole, triazole, tetrazole, and benzimidazole.

By way of further non-limiting example, the at least one organic amine is chosen from amino acid dipeptides. As amino acid dipeptides that may be used in the present disclosure, non-limiting mention may be made of carnosine, anserine, and baleine.

By way of further non-limiting example, the at least one organic amine may be chosen from compounds comprising a guanidine functional group. As amines of this type that may be used in the present disclosure, besides arginine that has already been mentioned as an amino acid, mention may be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

By way of non-limiting example, the at least one organic amine present in the at least one composition (B) according to the present disclosure may be an alkanolamine. For example, the at least one organic amine can be chosen from 2-amino-2-methyl-1-propanol and monoethanolamine. In at least one embodiment, the at least one organic amine is monoethanolamine.

The at least one organic amine can be present in composition (B) in an amount ranging from 0.1% to 40% by weight, for example from 0.5% to 20% by weight relative to the weight of said composition.

Composition (B) may be an aqueous or nonaqueous composition. As used herein, "aqueous composition" means a composition comprising more than 5% by weight of water, for example more than 10% by weight of water, and further for example more than 20% by weight of water.

In at least one embodiment, composition (B) is an aqueous composition.

Composition (B) may optionally comprise at least one organic solvent. Non-limiting examples of organic solvents that may be mentioned include linear and branched $C_2$-$C_4$ alkanols, such as ethanol and isopropanol, glycerol, polyols and polyol ethers, for instance 2-butoxyethanol, propylene glycol, dipropylene glycol, propylene glycol monomethyl ether, diethylene glycol monomethyl ether, and monoethyl ether, and also aromatic alcohols, for instance benzyl alcohol or phenoxyethanol, and mixtures thereof.

The at least one solvent, when it is present, may be present in a total amount ranging, for example, from 1% to 40% by weight, further for example from 5% to 30% by weight relative to the weight of the composition (B).

The process is also performed with at least one composition (C) comprising at least one oxidizing agent.

For example, the at least one oxidizing agent can be chosen from hydrogen peroxide, urea peroxide, alkali metal bromates and ferricyanides, and peroxygenated salts, for instance alkali metal and alkaline-earth metal persulfates, perborates and percarbonates, and peracids and precursors thereof.

In at least one embodiment the at least one oxidizing agent is constituted by hydrogen peroxide, such as an aqueous solution (aqueous hydrogen peroxide solution), the titre of which may range for example from 1 to 40 volumes and further for example from 5 to 40 volumes.

As a function of the desired degree of lightening, the at least one composition (C) may also comprise at least one oxidizing agent chosen from peroxygenated salts.

In at least one embodiment, the at least one oxidizing agent is not chosen from peroxygenated salts, peracids, and precursors thereof.

The at least one composition (C) according to the present disclosure may be aqueous or nonaqueous. As used herein, "aqueous composition" means a composition comprising more than 5% by weight of water, for example more than 10% by weight of water, and further for example more than 20% by weight of water.

In at least one embodiment, the at least one composition (C) is an aqueous composition.

The at least one composition (C) may also comprise at least one organic solvent.

Non-limiting examples of organic solvents that may be mentioned include linear and branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether, and monoethyl ether, and also aromatic alcohols, for instance benzyl alcohol and phenoxyethanol, and mixtures thereof.

When they are present, the at least one solvent may be present in a total amount ranging, for example, from 1% to 40% by weight, further for example from 5% to 30% by weight relative to the weight of the at least one composition (C).

The at least one composition (C) may comprise at least one acidifying agent.

Non-limiting examples of acidifying agents that may be mentioned include mineral and organic acids, for instance hydrochloric acid, orthophosphoric acid, sulfuric acid, carboxylic acids, for instance acetic acid, tartaric acid, citric acid, or lactic acid, and sulfonic acids.

The pH of the at least one composition (C), when it is aqueous, may be less than 7.

The at least one composition (C) may also contain other ingredients conventionally used in the field, including those detailed previously in the context of the anhydrous composition (A).

The at least one composition (C) may be in various forms, for instance a solution, an emulsion, or a gel.

According to one aspect of the present disclosure, a composition obtained by extemporaneously mixing, at the time of use, of the abovementioned at least one anhydrous composition (A), at least one composition (B), and at least one composition (C), is applied to wet or dry keratin fibers.

The value of the weight ratio R1 of the amounts of compositions ((A)+(B))/(C) and the value of the weight ratio R2 of the amounts of compositions (A)/(B) range from 0.1 to 10, for example from 0.3 to 3.

In accordance with at least one embodiment of the process, compositions (A), (B), and (C) are applied to the wet or dry keratin fibers, successively and without intermediate rinsing.

In at least one embodiment, compositions (B), (A), and (C) are applied successively and without intermediate mixing.

In at least one embodiment, composition (C) and the mixture resulting from compositions (A) and (B) are also applied successively and without intermediate rinsing.

In the previous two non-limiting embodiments, the value of the weight ratio R1 of the amounts of compositions ((A)+(B))/(C) and the value of the weight ratio R2 of the amounts of compositions (A)/(B) range from 0.1 to 10, for example from 0.3 to 3.

The mixture present on the fibers (resulting either from the extemporaneous mixing of compositions (A), (B), and (C) or from the partial or total successive application thereof) is left on the fibers for a period of time sufficient for lightening the fibers. For example, the period of time may range from 1 minute to 1 hour, for instance from 5 minutes to 30 minutes.

The temperature during the process may range from room temperature (from 15 to 25° C.) to 80° C., for example from room temperature to 60° C.

After the treatment, the human keratin fibers are optionally rinsed with water, optionally washed with a shampoo and then rinsed with water, before being dried or left to dry.

If the composition applied to the hair (comprising compositions (A), (B), and (C)) comprises aqueous ammonia, then the aqueous ammonia may be present in an amount, for example, less than or equal to 0.03% by weight of the final composition (expressed as $NH_3$) and further for example less than or equal to 0.01% by weight relative to the final composition. The final composition results from the mixing of compositions (A), (B), and (C); these mixtures being prepared either before application to the keratin fibers (extemporaneous preparation) or directly on the keratin fibers (successive applications with or without premixing and without intermediate rinsing).

In at least one embodiment, compositions (A), (B), and (C) do not comprise aqueous ammonia.

Another aspect of the present disclosure relates to a multi-compartment device or kit comprising, in at least one first compartment, at least one anhydrous composition (A), in at least one second compartment, at least one composition (B) comprising at least one organic amine having a pKb at 25° C. less than 12, and, in at least one third compartment, at least one composition (C) comprising at least one oxidizing agent, these compositions having been described previously.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES

The following compositions were prepared:
Anhydrous composition (A): (the amounts are expressed in grams)

| Oxyethylenated (4 EO) sorbitan monolaurate | 21.67 |
| Fumed silica of hydrophobic nature | 11 |
| Liquid petroleum jelly | qs 100 |

Composition (B) comprising 40 g of monoethanolamine, the remainder to 100 g being water.

At the time of use, the following were mixed together:
9 parts by weight of the anhydrous composition (A)
1 part by weight of composition (B)
10 parts by weight of composition (C) comprising 6% hydrogen peroxide at pH 2.3 and comprising about 80% water.

The resulting mixture, having a pH of about 10, was applied to a lock of natural chestnut-brown hair (tone depth of 5).

The leave-on time was 30 minutes at room temperature (about 25° C.). After this leave-on time, the lock was rinsed and then washed with Elsève multivitamin shampoo.

For comparative purposes, the following aqueous ammonia-based composition was prepared (amounts expressed in g %):

| Comparative Example | |
|---|---|
| Oleyl alcohol polyglycerolated with 2 mol of glycerol | 4 |
| Oleyl alcohol polyglycerolated with 4 mol of glycerol | 5.69 AM |
| Oleic acid | 3 |
| Oleyl amine containing 2 mol of ethylene oxide (Ethomeen 012 from Akzo) | 7 |
| Diethylaminopropyl laurylaminosuccinamate, sodium salt (55% active material) | 3.0 AM |
| Oleyl alcohol | 5 |
| Oleic acid diethanolamide | 12 |
| Ethyl alcohol | 7 |
| Propylene glycol | 3.5 |
| Dipropylene glycol | 0.5 |
| Propylene glycol monomethyl ether | 9 |
| Ammonium acetate | 0.8 |
| 20% aqueous ammonia | 10 |
| Demineralized water qs | 100 g |

AM: amount expressed as active material

At the time of use, the comparative composition was mixed weight for weight with an aqueous composition (C) comprising 6% hydrogen peroxide at pH 2.3 and comprising about 80% water.

The mixture thus obtained, having a pH of about 10, was then applied to a lock of natural chestnut-brown hair (tone depth of 5).

The leave-on time was 30 minutes at room temperature.

After this leave-on time, the lock was rinsed and then washed with Elsève multivitamin shampoo.

The combined composition according to the present disclosure, did not give off any disagreeable odor, unlike the comparative composition, which gave off a strong odor of ammonia.

The table below shows that the combined composition according to the present disclosure, free of aqueous ammonia, gives a lightening result equivalent to that of the aqueous ammonia-based comparative composition. L* indicates the lightness. The lower the value of L*, the more intense is the color of the hair.

| | L* | ΔL* |
|---|---|---|
| Untreated lock of natural chestnut-brown hair (HT5) | 19.82 | — |
| Composition of the present disclosure | 25.70 | 5.88 |
| Composition of the prior art | 24.92 | 5.10 |

What is claimed is:

1. A process for lightening human keratin fibers, comprising:
   (a) applying to the fibers a mixture formed by extemporaneously mixing, at the time of use:
      at least one anhydrous composition (A) comprising at least one fatty substance and at least one surfactant,
      wherein the at least one fatty substance is liquid at a temperature of 25° C. and at atmospheric pressure, and
      wherein the at least one fatty substance is present in an amount ranging from 10% to 99% by weight, relative to the weight of the anhydrous composition (A);
   at least one composition (B) comprising at least one organic amine having a pKb less than 12; and
   at least one composition (C) comprising at least one oxidizing agent; and
   (b) leaving the mixture on the fibers for a period of time sufficient to lighten the fibers.

2. The process according to claim 1, wherein the at least one fatty substance is chosen from alkanes, fatty alcohols, fatty acids, fatty acid esters, fatty alcohol esters, mineral oils, plant oils, animal oils, synthetic oils, silicones, and waxes.

3. The process according to claim 1, wherein the at least one fatty substance is chosen from liquid petroleum jelly, polydecenes, and liquid esters.

4. The process according to claim 1, wherein the at least one surfactant is a nonionic surfactant chosen from monooxyalkeylenated, polyoxyalkylenated, monoglycerolated, and polyglycerolated nonionic surfactants.

5. The process according to claim 1, wherein the at least one surfactant is present in an amount ranging from 0.1% to 50% by weight relative to the weight of the anhydrous composition (A).

6. The process according to claim 1, wherein the at least one organic amine is at least partially miscible in the at least one fatty substance.

7. The process according to claim 1, wherein the at least one organic amine comprises one or two functional groups chosen from primary, secondary, and tertiary amine functional groups, and at least one group chosen from linear and branched $C_1$-$C_8$ alkyl group bearing at least one hydroxyl radical.

8. The process according to claim 1, wherein the at least one organic amine is chosen from:
   an alkanolamine chosen from mono-, di-, and trialkanolamines, comprising from one to three identical or different $C_1$-$C_4$ hydroxyalkyl radicals and a compound of formula:

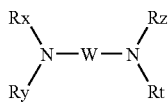

wherein W is chosen from $C_1$-$C_6$ alkylene residues optionally substituted with a hydroxyl group; Rx, Ry, Rz, and Rt which may be identical or different, are chosen from a hydrogen atom, $C_1$-$C_6$ alkyl, $C_1$-$C_6$ hydroxyalkyl, and $C_1$-$C_6$ aminoalkyl radicals.

9. The process according to claim 7, wherein the at least one organic amine is an alkanolamine.

10. The process according to claim 7, wherein the at least one organic amine is chosen form 2-amino-2-methyl-1-propanol and monoethanolamine.

11. The process according to claim 1, wherein the at least one organic amine is chosen from the amino acids of formula (I):

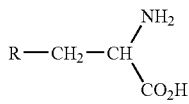

wherein R is a group chosen from:

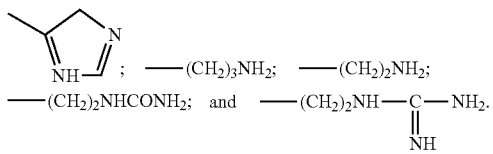

12. The process according to claim 11, wherein the at least one organic amine is chosen from arginine, histidine, and lysine.

13. The process according to claim 1, wherein the at least one organic amine is present in an amount ranging from 0.1% to 40% by weight relative to the weight of composition (B).

14. The process according to claim 13, wherein the at least one organic amine is present in an amount ranging from 0.5% to 20% by weight relative to the weight of composition (B).

15. The process according to claim 1, wherein the value of the weight ratio R1 of the amounts of compositions ((A)+(B))/(C), and the value of the weight ratio R2 of the amounts of compositions (A)/(B), range from 0.1 to 10.

16. A process for lightening human keratin fibers, comprising:
  (a) applying to the fibers:
    at least one anhydrous composition (A) comprising at least one fatty substance and at least one surfactant,
      wherein the at least one fatty substance is liquid at a temperature of 25° C. and at atmospheric pressure, and
      wherein the at least one fatty substance is present in an amount ranging from 10% to 99% by weight, relative to the weight of the anhydrous composition (A);
    at least one composition (B) comprising at least one organic amine having a pKb less than 12; and
    at least one composition (C) comprising at least one oxidizing agent;
    wherein:
      compositions (A), (B), and (C) are applied to the fibers successively and without intermediate rinsing, or
      compositions (B), (A), and (C) are applied to the fibers successively and without intermediate rinsing, or
      composition (C) and a mixture resulting from mixing compositions (A) and (B) are applied to the fibers successively and without intermediate rinsing;
  and
  (b) leaving the compositions on the fibers for a period of time sufficient to lighten the fibers.

* * * * *